United States Patent [19]

Kulprathipanja et al.

[11] Patent Number: 5,648,579

[45] Date of Patent: Jul. 15, 1997

[54] CONTINUOUS ALKYLATION OF AROMATICS USING SOLID CATALYSTS; PREVENTION OF CATALYST DEACTIVATION USING A PULSED FEED REACTOR

[75] Inventors: Santi Kulprathipanja, Inverness; Joseph A. Kocal, Gurnee; Stanley A. Gembicki, Clarendon Hills, all of Ill.

[73] Assignee: UOP, Des Plaines, Ill.

[21] Appl. No.: 392,006

[22] Filed: Feb. 21, 1995

Related U.S. Application Data

[63] Continuation-in-part of Ser. No. 126,416, Sep. 27, 1993, abandoned.

[51] Int. Cl.⁶ .................................................. C07C 15/067
[52] U.S. Cl. ........................................... 585/447; 585/446
[58] Field of Search ................................... 585/446, 447; 502/31

[56] References Cited

U.S. PATENT DOCUMENTS

| | | | |
|---|---|---|---|
| 3,851,004 | 11/1974 | Yang | 585/446 |
| 4,008,291 | 2/1977 | Zabransky et al. | 260/683.43 |
| 4,028,430 | 6/1977 | Stine et al. | 260/683.43 |
| 4,072,729 | 2/1978 | Stine et al. | 260/671 R |

*Primary Examiner*—Glenn Caldarola
*Assistant Examiner*—In Suk Bullock
*Attorney, Agent, or Firm*—Thomas K. McBride; Eugene I. Snyder

[57] ABSTRACT

A novel continuous process for the preparation of alkylated benzenes effected by solid catalysts which become deactivated under alkylation conditions uses a single catalyst zone for both reaction and catalyst flushing to prevent deactivation. The process utilizes a pulsed flow of the linear monoolefins into the catalyst zone during a reaction cycle with benzene acting as a desorbent for catalyst deactivating agents to prevent significant catalyst deactivation. The process can be generalized to encompass many types of reactions.

28 Claims, 3 Drawing Sheets

CONTINUOUS ALKYLATION OF AROMATICS USING SOLID CATALYSTS; PREVENTION OF CATALYST DEACTIVATION USING A PULSED FEED REACTOR

CROSS REFERENCE TO RELATED APPLICATION

This application is a continuation-in-part of our application, U.S. Ser. No. 08/126,416, filed Sep. 27, 1993, now abandoned, all of which is incorporated herewith.

BACKGROUND OF THE INVENTION

Over fifty years ago it was recognized that alkylbenzene sulfonates (ABS) were quite effective detergents superior to natural soaps in many respects. Because of their lower price, their price stability, and their effectiveness in a wide range of detergent formulations, ABS rapidly displaced soaps in household laundry and dishwashing applications and became the standard surfactants for the detergent industry.

The alkylbenzene sulfonates as initially prepared had substantial branching in the alkyl chain. This situation was maintained until the early 1960's when it became apparent that the branched alkyl-based detergents were contributing to the pollution of lakes and streams and forming relatively stable foams. Examination of the problem showed that the branched structure of the alkyl chains was not susceptible to rapid biodegradation and the surfactant properties of the detergent thus persisted for long periods of time. This was not the case earlier when natural soaps were used, because of the rapid biodegradation of the linear chains in natural soaps.

After recognizing the biodegradability of ABS based on alkylation by linear olefins, industry turned its attention to the production of these unbranched olefins and their subsequent use in the production of linear alkyl benzenes. Processes were developed for efficient alkylation of benzene by available feedstocks containing linear olefins, and the production of linear alkyl benzenes (LAB) became another reliable process broadly available to the petroleum and petrochemical industry. It gradually evolved that HF-catalyzed alkylation was particularly effective in LAB production, and an HF-based alkylation process became the industry standard. More recently solid acid catalysts have undergone intensive development as an alternative to liquid HF.

As desirable as solid catalysts may be as an alternative to liquid HF, a continuing impediment to their development has been their short lifetime. Although all catalysts lose some portion of their activity with continued use, the solid catalysts used to date in aromatic alkylation tend to deactivate rather quickly. Although their deactivation can be retarded by increasing alkylation reaction temperature, raising the reaction temperature tends to decrease product linearity, which is an undesirable outcome. Conversely, lowering the reaction temperature increases product linearity, an exceedingly desirable result, but exacerbates catalyst deactivation leading to useful catalyst lifetimes on the order of only several hours. Thus, it is clear that solid catalysts can be best used in the continuous alkylation of aromatics only where effective, convenient, and inexpensive means of catalyst regeneration are available.

Solid catalysts used for the alkylation of aromatic compounds by olefins, especially those in the 6–20 carbon atom range, usually are deactivated by byproducts which are preferentially adsorbed by the catalysts. Such byproducts include, for example, polynuclear hydrocarbons in the 10–20 carbon atom range formed in the dehydration of C6–C20 linear paraffins and also include products of higher molecular weight than the desired monoalkyl benzenes, e.g., di- and trialkyl benzenes, as well as olefin oligomers. Although it can be readily appreciated that such catalyst deactivating agents or "poisons" are an unavoidable adjunct of aromatic alkylation, hence catalyst deactivation also is unavoidable, fortunately it has been observed that the deactivating agents can be readily desorbed from the catalyst by washing the catalyst with the aromatic reactant. Thus, catalyst reactivation, or catalyst regeneration as the term is more commonly employed, is conveniently effected by flushing the catalyst with aromatic reactants to remove accumulated poisons from the catalyst surface, generally with restoration of 100% of catalyst activity. It would be particularly advantageous to integrate a continuous alkylation process with a method of removing catalyst deactivating agents virtually as formed, thereby preventing catalyst deactivation and obviating a separate catalyst regeneration stage. Our invention accomplishes this latter objective.

U.S. Pat. No. 4,028,430 describes a simulated moving bed reaction process which integrates catalyst regeneration and alkylation, as does U.S. Pat. No. 4,008,291 and 4,072,729. Description of only the '430 patent will suffice to illustrate the general teachings. The invention uses a fixed bed of solid catalyst containing four zones arranged in series with a fluid flow path connecting each adjacent zone as well as connecting the fourth zone to the first zone. The solid catalyst is one which deactivates due to adsorption onto the catalyst of higher molecular weight byproducts, but the solid catalyst can be readily reactivated by washing it with a suitable solvent to desorb these higher molecular weight deactivating materials.

The simulated moving bed reaction process as described operates in the following way. Reactants are introduced to the top of zone 1 and reaction products are withdrawn at the boundary of zones 1 and 2. A solvent known to effectively desorb from the catalyst those materials responsible for catalyst reactivation is introduced at the top of zone 3. In many cases the solvent is one of the reactants normally used in excess. Solvent flows from the top of zone 3 toward the bottom and a stream containing the desorbed material responsible for catalyst deactivation is withdrawn at the junction of zones 3 and 4. Since all or nearly all of the catalyst poisons are removed before zone 4, the catalyst in zone 4 is a reactivated or regenerated catalyst.

In practice the foregoing invention is performed using application of a simulated moving bed technique. In this technique the catalyst bed actually consists of a series of catalyst sub-beds, each with a fluid flow path connecting adjacent sub-beds, and means for shifting the points of inlet and outlet streams of the process. Thus the various distinct zones move spatially along the catalyst bed in a sort of circular fashion.

The foregoing process certainly has advantages which make it commercially the most preferred and profitable process for many reactions, nonetheless it is attended both by a high capital outlay and a relatively high operational cost. To reduce the process cost even further we have devised a process which accomplishes the same result as continuous alkylation with continuous catalyst regeneration using only a single catalyst zone where the input and output streams remain stationary relative to the catalyst bed. This obviates the need for construction of a relatively complex reactor, thus reducing capital costs, and the operational expense associated with our technique is more comparable to that of a conventional fixed bed reactor rather than a simulated moving bed reactor.

Our invention uses a single fixed bed catalyst zone where both alkylation and removal of catalyst deactivating agents occur. Reactants flow into the bed at or near one terminus of the catalyst zone along with desorbent. Reaction occurs along the catalyst bed and reaction products are collected at the second terminus of the catalyst zone. Our invention is characterized by a continuous flow of desorbent and a pulse flow of reactants. In a variant the desorbent flow is interrupted during at least a portion of the reactant flow pulse. In this way the materials causing catalyst deactivation are periodically collected at the second terminus of the catalyst bed, alternating with collection of products, and are thus removed from the catalyst bed with continuous maintenance of catalytic activity. Our process is simple, quite effective, and affords alkylated aromatic products of high quality.

Our process is distinguished from the prior art in two important ways. First is what may be termed a philosophical difference; whereas the prior art focuses attention on catalyst regeneration after deactivation, ours emphasizes prevention of deactivation. The second difference is a functional one; whereas the prior art may use a 2-cycle process (a reaction and a regeneration cycle) each of a relatively long duration, in our invention each cycle time is short, as is their sum or the periodicity of our process. Ancillary to this is the characteristic that the process of our invention requires only a single catalyst zone because of the short periodicity, whereas the prior art in practice requires at least two catalyst zones because the regeneration time (when no product is formed) is long.

The process which is our invention is characterized by two cycles: a reaction cycle, when both olefin and aromatic flow into the catalyst zone to effect alkylation, and a flush cycle when only a desorbent flows into the catalyst zone. For simplicity of exposition only we consider the case where the desorbent is also the aromatic being alkylated. In our process the periodicity is short, on the order of minutes, whereas the practice of the prior art utilizes a long periodicity measured in terms of several hours or even days. Periodicity can be expressed not only as time but equivalently in terms of fractional catalyst deactivation or fractional catalyst carbon buildup, and however the periodicity is expressed it is quite short—shorter by at least an order of magnitude—relative to the prior art practices of aromatic alkylation. Thus, a reaction cycle of about 10 minutes and a flush cycle of 10 minutes, to afford an overall periodicity of 20 minutes, is representative of our process and is clearly substantially different from prior art practice. A second distinguishing feature, easy to be overlooked at first glance, is that our process uses only a single catalyst bed in which both the reaction and regeneration cycles are effected sequentially and repeatedly. Thus, e.g., the prior art swing bed process utilizes at least two catalyst beds, one in which reaction is being effected and another in which regeneration is being effected concurrently. This obviously contrasts starkly with our invention, where both reaction and flushing are effected in the same catalyst bed sequentially (not concurrently) over a short time period, with the reaction-flushing cycle repeated essentially continuously until the catalyst bed is no longer usable. The foregoing also should make it clear that the relative times for the reaction and flush cycles will depend upon many factors, such as olefins used, the aromatic alkylated, reaction temperatures, aromatic to olefin ratio, and so on. But it should be equally clear that the periodicity and relative times of the reaction and flush cycles are readily within the purview of one skilled in the art and necessitate only a modicum of experimentation. Thus, optimization of the process of our invention requires only routine experimentation which the skilled worker will recognize.

However important and effective may be our process in the alkylation of aromatics to detergent alkylates, it is capable of broad generalization. Thus, although the principles elaborated below will be first specified with regard to detergent alkylation for the purpose of clarity and exemplification, it will be appreciated by the skilled worker that the principles are general and applicable to many reaction processes. It is to be clearly understood that our invention is not a narrow one, with the examples of its use increasing as the appreciation of its applicability increases.

SUMMARY OF THE INVENTION

A broad purpose of our invention is to make available an integrated process effecting continuous chemical reaction catalyzed by a bed of solid catalyst with prevention of catalyst deactivation using but a single catalyst zone. A narrower purpose is to make available a continuous process for the alkylation of benzene with detergent-range olefins using a solid catalyst which deactivates with continued use where the solid catalyst deactivation is prevented by alternating short reaction and flush cycles within the single reaction zone. An embodiment comprises leading a stream of benzene and a stream of linear monoolefins into one terminus of a bed of solid catalyst where the benzene and linear monoolefins react to form alkylated benzenes, withdrawing from the second terminus of the fixed bed of solid catalyst a stream of alkylated benzenes, periodically stopping the flow of linear monoolefins into the solid bed in order to desorb the deactivating agents from the solid catalyst with the benzene stream, and withdrawing from the second terminus of the bed of solid catalyst a stream enriched in catalyst deactivating agents and thereby preventing catalyst deactivation. Many other embodiments will become apparent from our ensuing description.

DETAILED DESCRIPTION OF THE INVENTION

Figure 1:
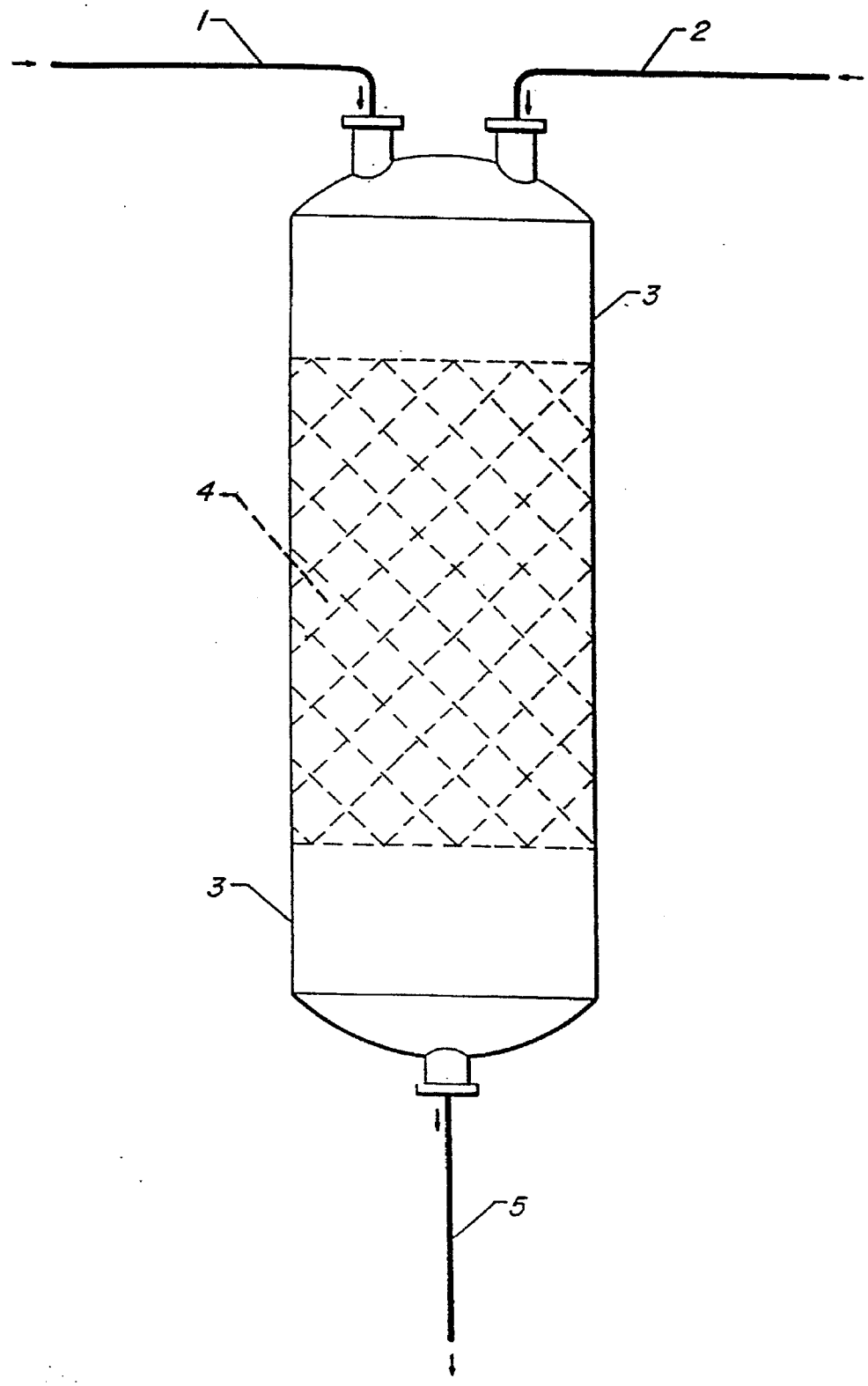
FIG. 1 is an overall, simplified and non-detailed depiction of a process flow in our invention.

Our invention can be most readily understood by reference to FIG. 1. Although FIG. 1 depicts a process where the fluid flow is downflow in the catalyst zone, the flow direction is unimportant to the success of our invention and our exposition as a downflow fluid flow is solely for convenience but otherwise bears no significance. The catalyst zone is generally indicated by 3 which is occupied by a fixed bed 4 of solid catalyst. Stream 1 enters the catalyst zone at or near the top. Stream 1 can be generally designated as the desorbent stream and continually flows through the catalyst zone in the most general variant of our invention. However, in another variant the flow of stream 1 is interrupted during at least part of the time that reactant(s) flow in stream 2. The desorbent is chosen so as to be effective in removing the deactivating materials from the solid catalyst. Stream 2 most generally contains the reactants, that is, the materials which react within the catalyst zone to afford the desired products.

However, in one important variant stream 1 can act as both a desorbent as well as a reactant. This will be seen most clearly in the specific examples which follow.

The reactants entering the catalyst zone in stream 2 undergo reaction in catalyst zone 3 as catalyzed by the bed of solid catalyst 4 and liquid flows along the catalyst zone finally to exit at or near the other terminus of the catalyst zone as stream 5 containing desorbent, products, and unchanged reactants. As reaction proceeds, catalyst deactivating agents, generally higher molecular weight materials formed as byproducts in the reaction or introduced along with reactants, are formed and accumulate on the catalyst. Because these are adsorbed on the solid catalyst more strongly than the reaction products, they tend to move through the reaction zone more slowly than the reaction product and are found most generally only to a minor amount when stream 5 is the reaction product stream.

Periodically stream 2 is halted and only the desorbent flows into the catalyst zone. During these periods the catalyst deactivating agents, in whole or in part, are desorbed from the solid catalyst and ultimately exit in stream 5. Thus, stream 5 alternates between a product stream during what one might call its product withdrawal cycle, and a stream enriched in catalyst deactivating agents during what one might refer to as its poison removal cycle. It is important to recognize that stream 5 may be a reaction product stream during at least part of the time when only desorbent is flowing through the catalyst zone. Similarly, stream 5 may be in the poison removal mode during at least the initial period when reactants flow into the catalyst zone. What is meant to be expressed is that in general the reaction product and poison removal cycles do not have to be coincident with those times when reactants flow into the catalyst zone or when only desorbent flows into the catalyst zone, respectively.

The foregoing description clearly shows that the process alternates between a reaction cycle and a flush cycle. During the reaction cycle both desorbent and reactants flow into the catalyst zone with attendant product formation, whereas during the flush cycle only desorbent flows into the catalyst zone with attendant poisons removal. It also should be clear that whereas the greater part of reaction occurs during the reaction cycle, some reaction continues during at least the initial portion of the flush cycle. The terms "reaction cycle" and "flush cycle" apply to the incoming streams 1 and 2 as well as the catalyst zone itself, whereas the terms "product removal cycle" and "poisons removal cycle" refer to the effluent stream 5. As previously noted, the reaction and flush cycles need not be exactly coincident with the product and poison removal cycles, respectively, although usually the offset will be relatively small. Exemplifying the process with respect to detergent alkylation, stream 1 will be benzene which acts not only as the desorbent but as one of the reactants. Stream 2 contains linear monoolefins typically in the C6–C20 range, although those in the C8–C16 range are more common and those in the C10–C14 range are most common. Unsaturation may appear anywhere on the linear monoolefin chain; there is no requirement as to the position of the double bond, the only requirement being the linearity of the olefin. The stream 2 containing linear monoolefins generally results from the dehydrogenation of paraffins of like carbon number range and thus is largely a mixture of unreacted paraffins, linear monoolefins as described, small amounts of branched olefins, typically on the order of 1–3%, and occasionally polyolefins, although the polyolefins normally are reduced to the monoolefins prior to the feedstock reacting with benzene.

Although the stoichiometry of the alkylation reaction requires only one molar proportion of benzene per mole of total linear monoolefins, the use of a 1:1 mole proportion results in excessive olefin polymerization and polyalkylation. That is, the reaction product under such conditions would consist of not only the desired monoalkylbenzenes, but also would contain large amounts of the dialkylbenzenes, trialkylbenzenes, possibly higher polyalkylated benzenes, olefin dimers, trimers, etc., and unreacted benzene. On the other hand, it is desired to have the benzene:olefin molar ratio as close to 1:1 as possible to maximize benzene utilization. The actual molar proportion of benzene entering at 1 to total monoolefins entering at 2 during the reaction cycle will therefore have an important affect on both conversion and, perhaps more importantly, selectivity of the alkylation reaction. To carry out alkylation with the desired conversion, selectivity, and linearity of the resulting monoalkylbenzene typically requires during the reaction cycle a benzene:linear monoolefin molar ratio of from 5:1 up to as high as 30:1, although normally the process operates satisfactorily at a total benzene:linear monoolefins molar ratio in the reaction cycle between about 8:1 and about 20:1.

In one variant the benzene flow is continuous. In another variant the benzene flow is interrupted for at least a portion of the time that the linear monoolefins are introduced via stream 2. In the latter case the linear monoolefins react with benzene which is retained in the reaction zone.

During the reaction cycle the stream of benzene and linear monoolefins enters the catalyst zone which is filled with a bed of solid catalyst maintained at alkylation conditions. Many solid materials having activity as detergent alkylation catalysts are well known to those practicing the alkylation art and it is unnecessary to describe these materials here in any great detail. Examples of such solid alkylation catalysts, which are illustrative rather than exhaustive, include materials such as silica-aluminas, including fluorided silica-aluminas, crystalline aluminosilicates such as zeolites and molecular sieves, naturally occurring and synthetic clays, including pillared clays, sulfated oxides such as sulfated zirconia, traditional Friedel-Crafts catalysts, such as aluminum chloride and zinc chloride, and solid Lewis acids generally. Whatever the catalyst used, the catalyst zone will be maintained at alkylation conditions. Alkylation generally is performed at a temperature, T, affording at least 98% conversion of olefin, and generally over about 99%. The alkylation temperature will, of course, depend on the catalyst used but most generally will be in the range of 10°–200° C. Since detergent alkylation is desirably performed in the liquid phase, the minimum reaction pressure will depend upon alkylation temperature as well as the nature of the feedstock and is readily determined by the skilled worker. Any pressure above this minimum will suffice, i.e., the reaction pressure is a non-critical variable which has no significant effect on alkylation so long as alkylation is conducted in the liquid phase. Overall space velocities usually are in the range of 0.5–50 hr$^{-1}$.

The reaction products formed in the catalyst zone are withdrawn at 5 during its product withdrawal cycle. The aromatic byproducts formed in the alkylation reaction as well as aromatic byproducts which may be found in the linear monoolefin stream 2 generally deactivate the solid catalyst steadily, presumably by blocking their strong acid sites. After the linear monoolefin stream flows for some period, which we refer to as the reaction cycle, the flow of stream 2 is discontinued. Since one of the reactants is no longer present, no further reaction occurs at the top of the reaction zone and there begins a period, the flush cycle, during which only the desorbent in stream 1 flows over the catalyst in zone 3. During the flush cycle the catalyst deactivating agents, which are held more strongly on the bed of solid catalyst than are the reaction products, are slowly desorbed from the catalyst bed and move through the catalyst zone. Eventually the catalyst deactivating agent front moves out of the catalyst zone into the effluent zone and is removed in stream 5 during its poisons removal cycle. Desorption of the catalyst deactivating agents is the very essence of preventing catalyst deactivation, and at the end of the flush cycle the catalyst is virtually identical to fresh catalyst. At this time linear monoolefin flow is once more begun via stream 2 and one enters another reaction cycle. The result is that one has but a single catalyst zone with a continuous (or nearly so) flow of benzene, acting in part as a necessary reactant and in part as a desorbent, and a pulsed flow of linear monoolefins. The bed operates in a reaction mode for part of the time and in a flush mode for another part of the time, so that in a continuous process there is cycling between continuous alkylation of benzene by the linear monoolefins and continuous catalyst flushing.

As previously stated, the times of the reaction mode and flush mode constitute a distinguishing feature of our invention relative to the prior art. Thus, whereas the prior art operates in a reaction mode for hours, or even days, followed by a flush mode (serving to regenerate catalyst) also measured in hours, or even days, in our invention both reaction and flush modes are on the order of minutes, i.e., the periodicity or time for the process to go through both reaction and flush modes, is quite short relative to the prior art processes. Typically the periodicity is in the range of 10–60 minutes, and frequently the periodicity is 30 minutes or less. Within this period the apportionment between reaction and flush modes is dependent on such factors as benzene:olefin ratio, reaction temperature, and the particular catalyst used inter alia, although the division between reaction and flush modes under any particular set of reaction conditions can be readily determined with only a modicum of experimentation. Ratios of times in reaction mode to flush mode often are in the range 0.5 to about 2.0.

Although periodicity is perhaps most readily expressed and understood in terms of time, equivalent modes of expression are possible. Thus, we have determined the extent of carbon formation on catalyst as a function of time. In a more-or-less typical case there may be 0.6% carbon formed after 6 hours reaction time, 0.9–1.0% after 12 hours, and 1.2% after 24 hours. Our invention may be successfully practiced if the periodicity corresponds to a reaction mode time where there is no more than 0.1% carbon formation on the catalyst with a similar flush mode time. That is, the periodicity is not more than twice the time for accumulation of 0.1 weight percent carbon on the solid acid catalyst.

In the broader case where alkylation is not restricted to detergent alkylation the alkylating agent is an olefin, an alcohol, or an alkyl halide containing from 1 up to about 24 carbon atoms. Where the alkylating agent is an olefin the latter may be either branched or unbranched and also may be substituted with, for example, an aromatic substituent. Examples of suitable olefins include ethylene, propylene, the butenes, pentenes, hexenes, heptenes, octenes, nonenes, decenes, undecenes, dodecenes, tridecenes, tetradecenes, pentadecenes, hexadecenes, heptadecenes, octadecenes, nonadecenes, eicosenes, heneicosenes, docosenes, tricosenes, and tetracosenes. Further examples include styrene, phenylpropene, phenylbutene, phenylpentene, phenylhexene, and so forth.

Another class of alkylating agents which may be used in the practice of our invention are alcohols. Like the olefins, the alkyl chain in the alcohol may be branched or unbranched and the hydroxyl group may be found anywhere on the alkyl chain. That is, there is no particular requirement as to the spatial position of the hydroxyl moiety on the alkene chain. Examples of alcohols which may be successfully used in our invention include methanol, ethanol, propanol, butanol, pentanol, hexanol, heptanol, octanol, nonanol, decanol, undecanol, tetradecanol, and so forth. Especially relevant to this branch of the invention is methanol as the alcohol.

The last of the three classes of alkylating agents which may be frequently used in the practice of this invention are alkyl halides. Alkyl chlorides are probably the most widely used alkyl halides, but alkyl bromides also may be successfully used in the practice of our invention. As with alcohols, the paraffinic chain may be either branched or unbranched and the halogen may be found at any position along the chain. Suitable examples of alkyl halides include propyl chloride, propyl bromide, butyl chloride, butyl bromide, pentyl chloride, pentyl bromide, hexyl chloride, hexyl bromide, heptyl chloride, heptyl bromide, benzyl chloride, benzyl bromide, xylyl chloride, xylyl bromide, phenethyl chloride, phenethyl bromide, allyl chloride, allyl bromide, butenyl chloride, butenyl bromide, and so forth.

In the more general case the alkylating agent is reacted with an alkylatable aromatic compound. Such aromatic compounds are selected from the group consisting of benzene, naphthalene, anthracene, phenanthrene, and substituted derivatives thereof. The most important class of substituents are alkyl moieties containing from 1 up to about 20 carbon atoms. Another important substituent is the hydroxyl moiety as well as the alkoxy moiety whose alkyl group also contains from 1 up to 20 carbon atoms. Where the substituent is an alkyl or alkoxy group, a phenyl moiety also can be substituted on the paraffinic chain. Although unsubstituted and monosubstituted benzenes, naphthalenes, anthracenes, and phenanthrenes are most often used in the practice of this invention, polysubstituted aromatics also may be employed. Examples of suitable alkylatable aromatic compounds include benzene, naphthalene, anthracene, phenanthrene, biphenyl, toluene, xylene, ethylbenzene, phenol, anisole, propylbenzene, butylbenzene, pentylbenzene, hexylbenzene, heptylbenzene, octylbenzene, and so forth; anisole, ethoxy-, propoxy-, butoxy-, pentoxy-, hexoxybenzene, and so forth.

In the more general case, there is a wide variation in the alkylation conditions of an alkylatable aromatic compound by an alkylating agent depending upon the reactivity of the two reactants. For example, for hydroxy benzenes (phenols) the hydroxyl moiety is found to be a quite activating group toward alkylation, and therefore the hydroxy benzenes are readily alkylated so that temperatures of no more than about 150° C. suffice. On the other hand, where the aromatic is an unsubstituted aromatic, such as benzene, and the alkylating agent is a lower olefin, such as propylene, temperatures as high as 400° C. may be necessary. Consequently, the temperature range appropriate for alkylation will be between about 10 and about 400° C., with the most usual temperature range being between 100° and 225° C. As regards pressures, since the alkylation is desirably conducted as a liquid phase process the reaction pressure must be sufficient to maintain the reactants in the liquid stage. This is the sole pressure requirement for the practice of this invention, and since a wide variety of alkylatable aromatics compounds and alkylating agents may be used in the practice of this invention it can be readily appreciated that there exists a wide variation in reaction pressure, from atmospheric up to as high as about 2000 pounds per square inch (14,000 kPa).

At this point it should be apparent that our invention is capable of broad generalization and may be applied to a wide class of processes. As additional examples of alkylation may be mentioned ethylbenzene production, where benzene is the desorbent and also one of the reactants (stream 1) and ethylene is the other reactant (stream 2), and cumene production, which differs from the foregoing only in that propylene replaces ethylene. Another example is that of olefin hydration generally, where olefins react with water. Whether the olefin is used also as the desorbent, or olefin is used only as a reactant in stream 2 along with water (and optionally a solvent) and a different material is used as the desorbent in stream 1 will depend on the solid acid catalyst used, hydration conditions, and the particular olefin being hydrated. Etherification (reaction of olefins with alcohols) is analogous to hydration and illustrates yet another reaction for which our process is applicable. Esterification is another example, where the reactants of organic acid and alcohol most likely would be in stream 2 and a different material would act as desorbent in stream 1. Another commercially important process for which our method has great potential is that of motor fuel alkylation, which may be broadly defined as the alkylation of C3–C6 olefins with alkanes in the C4–C6 range. In the most likely variant the desorbent would be another hydrocarbon, such as an aromatic or higher alkane, and the stream 2 would contain the reactant alkenes and alkanes. The foregoing examples are merely illustrative of the processes for which our invention are applicable and are not intended to be exhaustive in any way.

The following merely illustrates our invention and does not limit it in any way.

EXAMPLES

Demonstration of Operability

In this example the detergent alkylation reaction was carried out using a fluorided silica-alumina catalyst (see U.S. Pat. No. 5,196,574) to demonstrate the ability of a catalytic reaction cycle and a desorbent flush cycle to form product. The test was run at 150° C. using a 70 ml reactor column and a pressure of 100 psi. In this experiment, benzene desorbent was passed up-flow to the reactor column at a liquid hourly space velocity (LHSV) of about 1 for 1 hour. Benzene was stopped and a 10 ml mixed olefin feed was introduced into the reactor column at a rate of 1 LHSV. The olefin feed had the following composition:

TABLE 1

| Commercial Alkylation Feedstock Composition | |
|---|---|
| Linear paraffins and olefins | wt. % |
| C-10 | 13.7 |
| C-10 = | 1.7 |
| C-11 | 26.1 |
| C-11 = | 3.5 |
| C-12 | 22.2 |
| C-12 = | 3.3 |
| C-13 | 14.9 |
| C-13 = | 2.8 |
| C-14 | 5.1 |
| C-14 = | 0.1 |
| Aromatics | 5.2 |
| Others | 1.4 |

The benzene stream flow then was resumed at a rate of 1 LHSV and continued until all of the reaction products, deactivating agents (which in this case are heavy alkylates) and unreacted components have been eluted from the reactor column. The gas chromatographic analysis of the effluents are summarized in Table 2.

TABLE 2

| COMPONENT | WEIGHT PERCENT BY GC |
|---|---|
| Decylbenzene | 14.2 |
| Undecylbenzen | 28.3 |
| Dodecylbenzene | 26.3 |
| Tridecylbenzene | 21.5 |
| Tetradecylbenzene | 0.7 |
| Nonlinear AlkylBenzenes (Total) | 9.0 |

Figure 2:
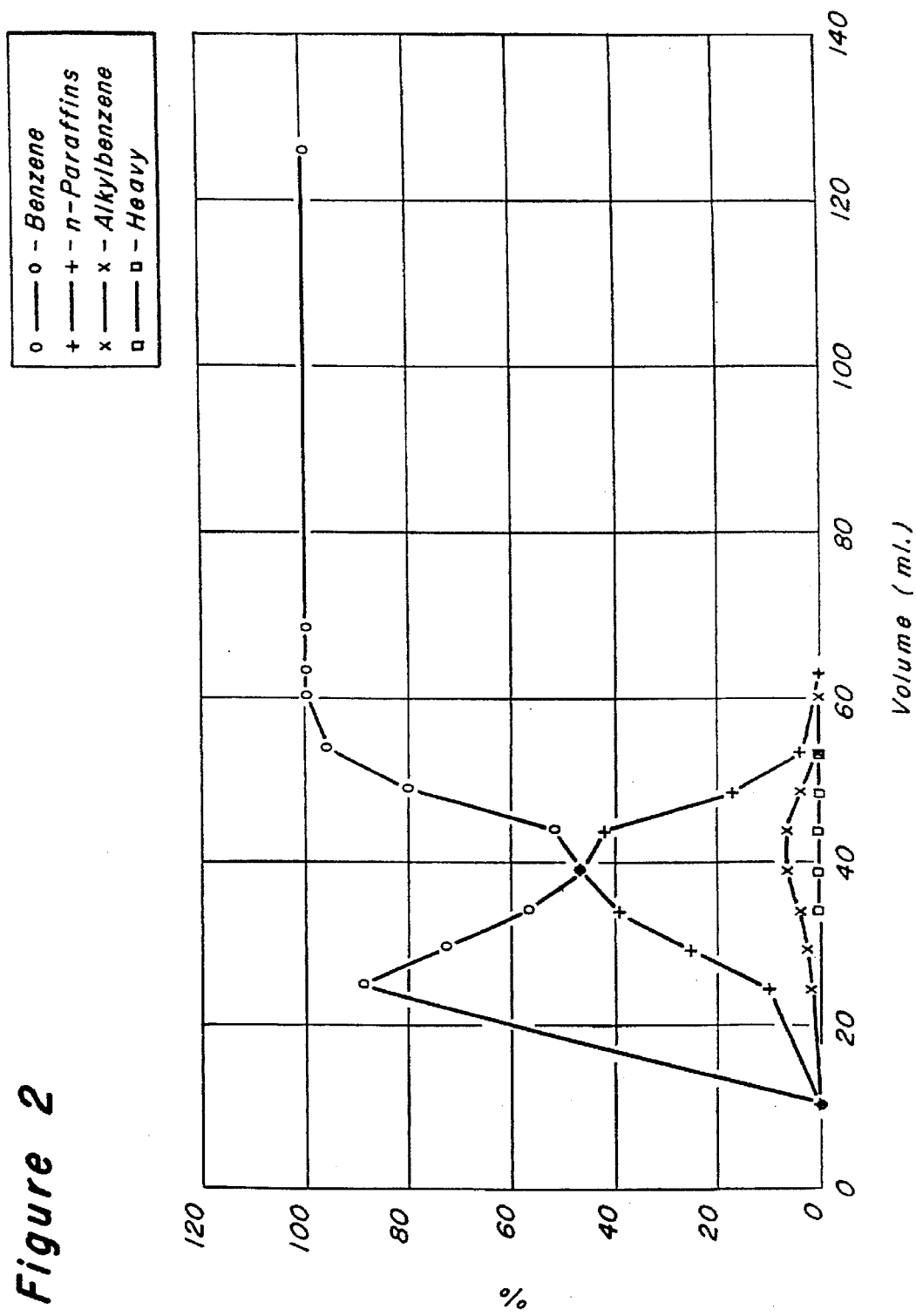
FIG. 2 is a gas chromatographic analysis of the effluents in the Demonstration of Operability example.

The result of the study is graphically shown in FIG. 2. No heavy alkylates trailing is observed in the experiment. This indicates that desorbent benzene is able to remove any poisons in the "poisons removal cycle", i.e., flush cycle.

Repeated Pulsing of Olefins

Figure 3:
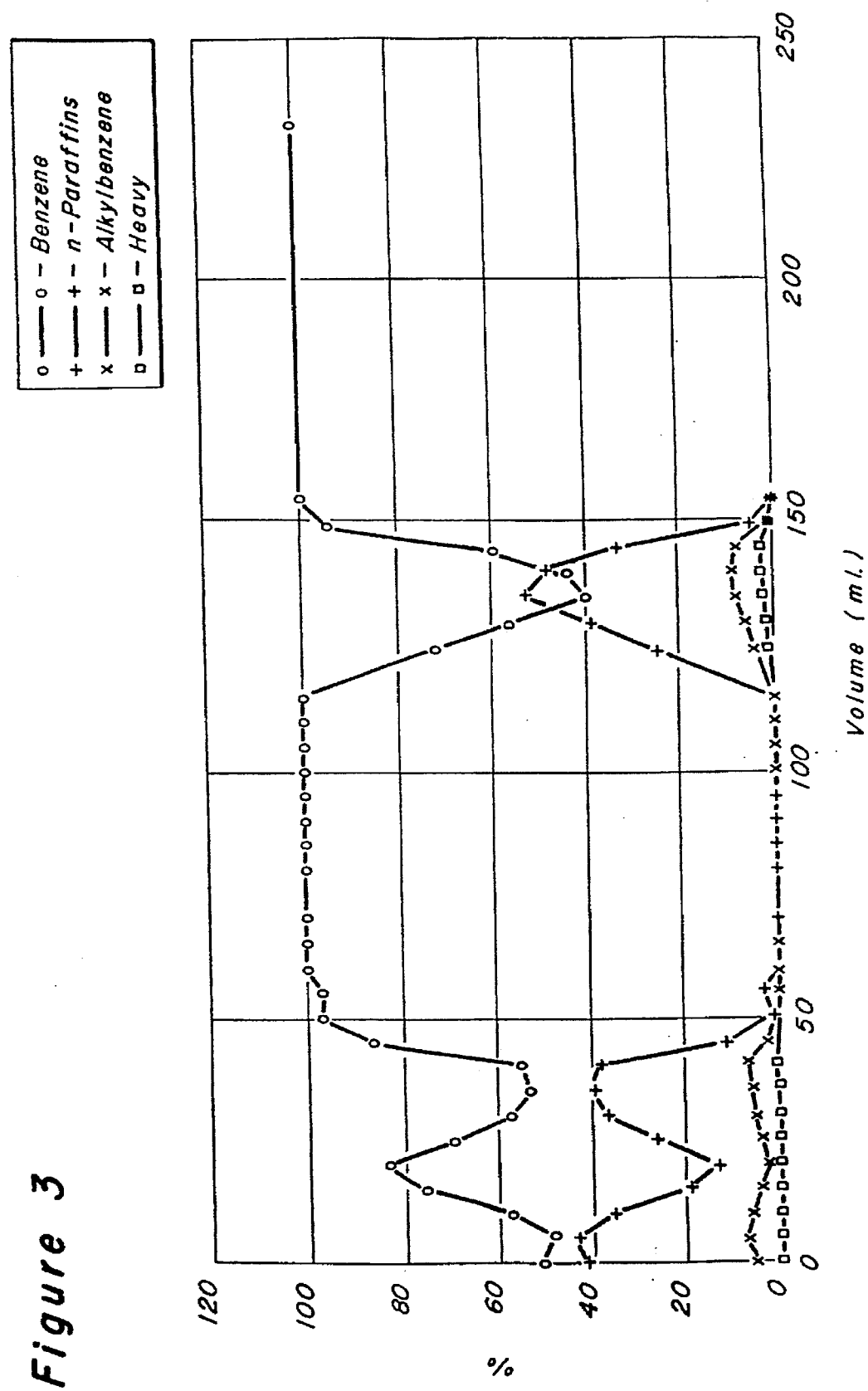
FIG. 3 is a gas chromatographic analysis of the effluents in the Repeated Pulsing of Olefins example.

In this example the above procedure was repeated ten times in the same catalyst bed to determine the repeated "poisons removal cycle" ability of benzene desorbent. Results of the last 2 pulses are summarized in FIG. 3. Again, no heavy alkylates trailing was observed at the end of the study and the catalyst activity is still maintained after 10 cycles of reaction and flushing. This result confirms our invention on prevention of catalyst deactivation using a pulsed feed reactor.

Pulse Frequency Adjustment

This example is run at conditions identical to the previous two examples with the change that the time between pulsing the olefin reactant was adjusted so that the reactor effluent was separated into two relatively pure product streams of monoalkylbenzene (desired product) and heavy alkylate (deactivating material). Operation in this manner would be very cost effective and a vacuum distillation column which is needed in the usual swing bed mode of operation to separate monoalkylbenzene and heavy alkylate will be eliminated. As a result the capital cost and considerable operating expense of this high temperature vacuum column are eliminated. Representative conditions may be exemplified by the following cases. In one, the feedstock during reaction contains benzene and an olefin mixture of average olefin molecular weight 168 was introduced during the reaction cycle at a benzene:olefin molar ratio of 9.3, with a reaction mode time of 8.3 minutes followed by a benzene flush time of 8.3 minutes, to give an overall benzene:olefin ratio of 19.6. In a second case the feedstock during reaction had a benzene:olefin ratio of 9.39, with a reaction and flush mode times of 8.3 and 10.4 minutes, resp., to give an overall benzene:olefin ratio of 22.4. In a third case the reaction mode feedstock has a benzene:olefin ratio of 11.1, with reaction and flush mode times of 8.3 and 12.5 minutes, resp., to give an overall benzene:olefin ratio of 29.3. In such cases no catalyst deactivation may be observed over long periods of time.

What is claimed is:

1. A method of continuously alkylating an aromatic compound with a linear monoolefin in the presence of a solid acid catalyst while preventing deactivation of said solid acid catalyst by alternating an alkylation mode for a time period $t_1$ with a flush mode for a time period $t_2$ in a single catalyst zone over a cycle of periodicity, $t_1+t_2$: where said alkylation mode comprises flowing at alkylating reaction conditions a mixture of an aromatic compound and at least one linear monoolefin into said catalyst zone, where said flush mode comprises flowing the aromatic compound in the absence of a linear monoolefin into said catalyst zone, and where the periodicity of the complete cycle of alkylation and flush modes is between about 10 minutes and one hour.

2. The process of claim 1 where the molar ratio of benzene to linear monoolefins in the reaction mode is from about 5 to about 30.

3. The process of claim 2 where the ratio is from about 8 to about 20.

4. The process of claim 1 where the linear monoolefins have from about 6 up to about 20 carbon atom.

5. The process of claim 4 where the linear monoolefins have from about 8 to about 16 carbon atoms.

6. The process of claim 5 where the linear monoolefins have from about 10 up to about 14 carbon atoms.

7. The process of claim 1 where the solid acid catalyst is selected from the group consisting of silica-aluminas, fluorided silica-aluminas, crystalline aluminosilicates, clays, sulfated oxides, and solid Lewis acids.

8. The method of claim 1 where the periodicity corresponds to the time not more than twice that needed for accumulation of 0.1 weight percent carbon on the catalyst.

9. A continuous process for the alkylation of benzene with linear monoolefins catalyzed by a fixed bed of solid catalyst at alkylation reaction conditions using a single catalyst zone having a first and second terminus, where said solid catalyst becomes deactivated through accumulation of deactivating agents under alkylation reaction conditions, comprising:

flowing a stream of benzene into the first terminus;

periodically flowing a stream of linear monoolefins into the first terminus and interrupting the flow of the benzene stream for at least a portion of the linear monoolefins stream flow;

reacting in the catalyst zone benzene with the linear monoolefins to form alkylated benzenes in a reaction cycle;

withdrawing from the second terminus a stream of alkylated benzenes;

desorbing the deactivating agents from the solid catalyst with the stream of benzene in a flush cycle; and withdrawing from the second terminus a stream enriched in deactivating agents so as to prevent catalyst deactivation.

10. The process of claim 9 where the molar ratio of benzene to linear monoolefins in the reaction cycle is from about 5 to about 30.

11. The process of claim 10 where the ratio is from about 8 to about 20.

12. The process of claim 9 where the linear monoolefins have from about 6 up to about 20 carbon atoms.

13. The process of claim 12 where the linear monoolefins have from about 8 to about 16 carbon atoms.

14. The process of claim 13 where the linear monoolefins have from about 10 up to about 14 carbon atoms.

15. The process of claim 9 where the solid catalyst is selected from the group consisting of silica-aluminas, fluorided silica-aluminas, crystalline aluminosilicates, clays, sulfated oxides, and solid Lewis acids.

16. The process of claim 9 where the total of reaction and flush cycles is no more than about 60 minutes.

17. A process for effecting cyclically and continuously in a single catalyst zone containing a solid catalyst a) a reaction effected by the catalyst where said catalyst undergoes deactivation during the course of the reaction and b) prevention of reactivation of said catalyst comprising:

flowing a first fluid stream of a desorbent into the catalyst zone;

flowing into said catalyst zone a second fluid stream containing at least one reactive component capable of reacting to form products in the presence of said solid catalyst;

reacting the reactive components in the catalyst zone to form products and accumulating in the catalyst zone agents serving to deactivate the catalyst;

withdrawing from the catalyst zone a stream enriched in products;

intermittently ceasing the flow of the second fluid stream into the catalyst zone;

desorbing from the solid catalyst the agents serving to deactivate the catalyst; and withdrawing from the catalyst zone the agents serving to deactivate the catalyst.

18. The process of claim 17 further characterized in that the flow of the desorbent stream flow is interrupted for at least a portion of the time of the second fluid stream flow.

19. The process of claim 18 where the desorbent is also a reactive component.

20. A continuous process for the alkylation of an alkylatable aromatic compound with an alkylating agent catalyzed by a fixed bed of solid catalyst at alkylation reaction conditions where said solid catalyst becomes continually deactivated under alkylation reaction conditions and using a single catalyst zone to effect catalytic reaction and to prevent catalyst deactivation comprising:

flowing a stream of alkylatable aromatic compound and a stream of alkylating agent into the catalyst zone in a reaction cycle;

reacting in the catalyst zone the alkylatable aromatic compound with the alkylating agent to form alkylated aromatic compound;

withdrawing from the catalyst zone a stream of alkylated aromatic compounds;

periodically interrupting the flow of the stream of alkylating agent into the catalyst zone in a catalyst flushing cycle to prevent accumulation of catalyst deactivating agents;

desorbing the deactivating agents from the solid catalyst with the stream of alkylatable aromatic compound; and withdrawing from the second terminus a stream enriched in deactivating agents so as to prevent catalyst deactivation.

21. The process of claim 20 further characterized in that the flow of the alkylatable aromatic compound stream is interrupted for at least a portion of the time of the alkylating agent stream flow.

22. The process of claim 20 where the alkylatable aromatic compound is selected from the group consisting of benzene, naphthalene, anthracene, phenanthrene, and benzene, naphthalene, anthracene, and phenanthrene bearing at least one substituent selected from the group consisting of alkyl, hydroxy, alkoxy, phenyl, and phenylalkyl, where each alkyl and alkoxy group contains from 1 up to about 21 carbon atoms.

23. The process of claim 22 where the alkylatable aromatic compound is benzene.

24. The process of claim 22 where the alkylatable aromatic compound is toluene.

25. The process of claim 22 where the alkylatable aromatic compound is hydroxybenzene.

26. The process of claim 22 where the alkylatable aromatic compound is an alkoxybenzene.

27. The process of claim 20 where the alkylating agent is an olefin, an alcohol, or an alkyl halide containing from 1 up to about 26 carbon atoms.

28. The process of claim 20 where the solid catalyst is selected from the group consisting of silica-aluminas, fluorided silica-aluminas, crystalline aluminosilicates, clays, sulfated oxides, and solid Lewis acids.

* * * * *